US011325149B2

(12) United States Patent
Tan et al.

(10) Patent No.: US 11,325,149 B2
(45) Date of Patent: May 10, 2022

(54) ULTRASONIC ATOMIZER AND CARTRIDGE FOR THE DISPERSAL OF A LIQUID

(71) Applicants: William Tan, San Gabriel, CA (US); Liat Keng Kang, Singapore (SG)

(72) Inventors: William Tan, San Gabriel, CA (US); Liat Keng Kang, Singapore (SG)

( * ) Notice: Subject to any disclaimer, the term of this patent is extended or adjusted under 35 U.S.C. 154(b) by 543 days.

(21) Appl. No.: 16/414,776

(22) Filed: May 16, 2019

(65) Prior Publication Data

US 2020/0009600 A1 Jan. 9, 2020

Related U.S. Application Data

(63) Continuation-in-part of application No. PCT/US2018/045885, filed on Aug. 8, 2018, and a continuation-in-part of application No. 15/472,223, filed on Mar. 28, 2017, now abandoned, and a continuation-in-part of application No. 15/004,920, filed on Jan. 23, 2016, now abandoned.

(60) Provisional application No. 62/672,555, filed on May 16, 2018.

(51) Int. Cl.

| | |
|---|---|
| *B05B 17/06* | (2006.01) |
| *A61M 11/00* | (2006.01) |
| *A61M 11/04* | (2006.01) |

(52) U.S. Cl.
CPC ....... *B05B 17/0684* (2013.01); *A61M 11/005* (2013.01); *A61M 11/04* (2013.01); *B05B 17/0623* (2013.01); *A61M 2205/6009* (2013.01); *B05B 17/0661* (2013.01)

(58) Field of Classification Search
CPC .... A24F 47/002; A61M 11/04; A61M 11/041; A61M 11/042; A61M 11/005–007; A61M 15/00; A61M 15/001; A61M 15/0021; A61M 15/0085; A61M 15/06; A61M 2205/3693; A61M 2205/8206; B05B 17/00–0684; B06B 1/06; B06B 1/0607; B06B 1/0611

USPC .................................................... 128/200.16

See application file for complete search history.

(56) References Cited

U.S. PATENT DOCUMENTS

| | | | | |
|---|---|---|---|---|
| 4,085,893 | A | 4/1978 | Durley | |
| 4,334,531 | A * | 6/1982 | Reichl | A61M 15/00 128/200.14 |
| 4,474,191 | A | 10/1984 | Steiner | |

(Continued)

FOREIGN PATENT DOCUMENTS

| | | | |
|---|---|---|---|
| GB | 2107611 | A | 5/1983 |
| WO | 2008015394 | A1 | 2/2008 |

OTHER PUBLICATIONS

U.S. Appl. No. 61/921,906, filed Dec. 30, 2013; Inventor Tan.

(Continued)

*Primary Examiner* — Elliot S Ruddie

(74) *Attorney, Agent, or Firm* — Law Office of David Hong

(57) ABSTRACT

The apparatus has an atomizer for the dispersal of a liquid and has an enclosed removable cartridge assembly with a reservoir of liquid and a wick with one end in communication with the liquid and a vibrating transducer in contact with another end of the wick; the transducer, wick and cartridge of liquid are arranged to allow a capillary volume of liquid from the wick to vibrate together to disperse the liquid in a direction away from the wick.

9 Claims, 6 Drawing Sheets

(56) References Cited

U.S. PATENT DOCUMENTS

| | | |
|---|---|---|
| 4,848,376 A | 7/1989 | Lilja |
| 4,877,989 A | 10/1989 | Drews |
| 4,922,901 A | 5/1990 | Brooks |
| 5,274,214 A | 12/1993 | Blackburn |
| 5,702,360 A | 12/1997 | Dieras |
| 5,950,619 A | 9/1999 | Van Der Linden |
| 6,278,218 B1 | 8/2001 | Madan |
| 7,052,468 B2 | 5/2006 | Melker |
| 7,337,776 B2 | 3/2008 | Fishman |
| 7,681,572 B2 | 3/2010 | Fishman |
| 7,784,712 B2 | 8/2010 | Wang |
| 7,975,688 B1 | 7/2011 | Truitt |
| 8,061,629 B2 * | 11/2011 | Tranchant ........... B05B 17/0623 239/102.2 |
| 8,257,377 B2 | 9/2012 | Wiener |
| 8,794,231 B2 | 8/2014 | Thorens |
| 8,910,639 B2 | 12/2014 | Chang |
| 2007/0102013 A1 | 5/2007 | Adams |
| 2008/0092912 A1 | 4/2008 | Robinson |
| 2009/0065600 A1 | 3/2009 | Tranchant |
| 2010/0044460 A1 | 2/2010 | Sauzade |
| 2011/0094523 A1 | 4/2011 | Thorens |
| 2014/0041658 A1 | 2/2014 | Goodman |
| 2014/0270727 A1 | 9/2014 | Ampolini |
| 2014/0270730 A1 | 9/2014 | DePiano |
| 2016/0213866 A1 * | 7/2016 | Tan .................. A61M 11/005 |

OTHER PUBLICATIONS

U.S. Appl. No. 61/928,823, filed Jan. 17, 2014; Inventor Tan.
U.S. Appl. No. 61/928,797, filed Jan. 17, 2014; Inventor Tan.
U.S. Appl. No. 14/271,442, filed May 6, 2014; Inventor Tan.
U.S. Appl. No. 13/188,450, filed Jul. 21, 2011; Inventor: Lee, C.
U.S. Appl. No. 61/366,603, filed Jul. 22, 2010; Inventor: Lee, C.
U.S. Appl. No. 61/748,530, filed Jan. 3, 2013; Inventors: Lee and Tan.
U.S. Appl. No. 14/272,249, filed May 7, 2014; Inventor Tan.
U.S. Appl. No. 14/272,414, filed May 7, 2014; Inventor Tan.
U.S. Appl. No. 62/106,852, filed Jan. 23, 2015; Inventor Tan; "ultrasonic vaporizing element."
U.S. Appl. No. 62/142,464, filed Apr. 2, 2015; Inventor Tan; "ultrasonic vaporizing element."
U.S. Appl. No. 15/004,920, filed Jan. 23, 2016; Inventor Tan; "ultrasonic vaporizing element."
U.S. Appl. No. 62/314,380, filed Mar. 28, 2016; Inventors Tan and Kang; "ultrasonic vaporizing alement."
U.S. Appl. No. 62/343,086, filed May 30, 2016; Inventor Tan; "ultrasonic vaporizing element with wickless delivery system".
U.S. Appl. No. 62/050,068, filed Sep. 12, 2014; Inventors Tan & Kang; "apparatus for power regulation."
Prokic, Miodrag, et. al. "The Ultrasonic Hammer Transducer." Internet printout from http://www.mpi-ultrasonics.com/content/ultrasonic-hammer-transducer, 2001.
U.S. Appl. No. 62/672,555, filed May 16, 2018; Inventors Tan & Kang; "Improvements for Ultrasonic Atomizer and Cartridge for the Dispersal of a Liquid."
U.S. Appl. No. 15/472,223, filed Mar. 28, 2017; Inventor Tan; "Improvement for ultrasonic vaporizing element."

* cited by examiner

ULTRASONIC ATOMIZER AND CARTRIDGE FOR THE DISPERSAL OF A LIQUID

This application claims the benefit of U.S. Provisional Patent Appl. No. 62/672,555, filed on May 16, 2018; this application is a continuation in part of U.S. patent application Ser. No. 15/472,223, filed on Mar. 28, 2017, a continuation in part of U.S. patent application Ser. No. 15/004,920, filed on Jan. 23, 2016 and a continuation in part of PCT/US2018/045885, filed on Aug. 8, 2018; this application is related to U.S. Provisional Patent Appl. No. 62/542,715, filed on Aug. 8, 2017; 62/106,852, filed on Jan. 23, 2015; 62/142,464, filed on Apr. 2, 2015; PCTUS2016014646, filed on Jan. 23, 2016; U.S. Provisional Patent Appl. No. 62/314,380, filed on Mar. 28, 2016; U.S. Provisional Patent Appl. No. 62/343,086, filed on May 30, 2016, which are all incorporated by reference in entirety.

BACKGROUND OF THE INVENTION

1. Field of the Invention

The present invention relates to an atomizer for the dispersal of a liquid.

2. Description of Related Art

Atomizers for dispensing of liquids are well known in the art. A common ultrasonic atomizer such as SC Johnson's Glade Wisp air freshener typically comprises a wick which is placed in the reservoir of material to be dispensed. The wick leads to a position adjacent to a vibrating plate which is provided with a plurality of fine holes. Liquid from the wick is held in a gap between the wick and plate. As the plate is vibrated, this liquid is dispersed through the holes in the orifice plate.

Cartridge with pre-filled liquid fragrance can be replaced when the old ones are used up. However, the mesh plate is permanently attached to the transducer and cannot be easily removed for cleaning. When the atomizer is not used for a long period of time, the fine holes on the plates may be clogged with dried particulates, diminishing vapor output.

The Omron NE-U22 medical nebulizer is another example of the use of a vibrating mesh. The mesh is spaced from the transducer with a gap between the two. This gap provides a capillary space along which liquid medicine flows in order to cover the surface of the transducer. As the transducer vibrates, it pushes the liquid through the orifices in the mesh thereby dispensing the medicine for inhalation.

The mesh plate in the Omron NE-U22 nebulizer is attached to a liquid reservoir, which is designed to be removable and washable. However, it is troublesome to sterilize after each use. A sterile reservoir and mesh plate are important because of potential contamination of the inhalation medicine. Replacing the mesh plate after each use is also impractical due to the high cost of replacement parts.

Another example of a vibrating media is described in application PCT/GB2007/002863. Rather than a metallic mesh plate, the application describes the use of a wick made of a fibrous material, which is in contact with the transducer and vibrates with it. Liquid is drawn by the wick from a liquid reservoir and delivered to the transducer by capillary action. As the transducer vibrates, the acoustic energy from the transducer on one side of the wick causes liquid to disperse from the opposite side, away from the transducer.

The use of a fibrous material is better suited for a disposable design, as materials like cotton or polymer fiber wicks are easier and cheaper to manufacture than metal mesh plates. However, the fibrous material needs to be thin enough for the acoustic energy to sufficiently penetrate to atomize the liquid. A thick material will dampen the wave energy and affect vapor output. On the other hand, a thin material is ineffective in drawing sufficient liquid from the reservoir to be delivered to the transducer.

After the initial amount of material is atomized, the wick section adjacent to the transducer becomes dry. The atomizer needs to pause for several seconds for the wick to soak up enough liquid for the next cycle. This is obviously impractical in applications requiring constant vapor output, such as spray painting or inhalation of lung medication.

It is an object of the present invention to address one or more of the above-mentioned problems. In particular, it is an object of the present invention to provide an improved design of an atomizer. From the preceding descriptions, it is apparent that the devices currently being used have significant disadvantages. Thus, important aspects of the technology used in the field of invention remain amenable to useful refinement.

SUMMARY OF THE INVENTION

An apparatus for vaporizing a liquid using an ultrasonic transducer and a sealed cartridge with a wick; in one preferred embodiment, the apparatus has an atomizer for the dispersal of a liquid and has an enclosed removable cartridge assembly with a reservoir of liquid and a wick with one end in communication with the liquid and a vibrating transducer in contact with another end of the wick; the transducer, wick and cartridge of liquid are arranged to allow a capillary volume of liquid from the wick to vibrate together to disperse the liquid in a direction away from the wick; magnets or springs can help position and provide the proper orientation of the removable cartridge from a first position (non-operation) to a second position (operational); in the first position, the wick on the removable cartridge is not contacting the transducer probe; in the second position, the removable cartridge is moved and breaks the magnetic contact or compresses the spring so that the wick on the removable cartridge can engage and contact the transducer or transducer probe, which is then activated or powered up.

An assembly for vaporizing a liquid, comprising: an ultrasonic transducer with a vibrating transducer tip; a cartridge, which is airtight and holds the liquid; the cartridge has a wick, which has a first wick end and a second wick end; the first wick end is in communication with the liquid, and when the second wick end is in contact with the vibrating transducer tip or probe, capillary action draws the liquid out of the cartridge; when the ultrasonic transducer is activated or powered up, the liquid, which is drawn out though the capillary action of the wick, is atomized to create atomized liquid or a vapor, and cavitation occurs; said cavitation creates gas bubbles at the wick, forces said gas bubbles through the wick and into the cartridge and balances the pressure within the cartridge; whereby the ultrasonic transducer, the cartridge and the wick are arranged to allow the atomized liquid or the vapor to move in a direction away from the cartridge and the vibrating transducer tip.

The wick comprises a thin membrane of cotton, ceramic or glass fibers; the wick can also be a porous silicone membrane; the cartridge can be sealed, removable and can have an authentication chip to allow for verification of the cartridge for use with authorized types of vaporizers. In a first position, the cartridge's second wick end is not in contact with the vibrating transducer tip or probe; the cartridge is held in said first position with springs or magnets; wherein in a second position, the cartridge's second wick end is in contact with the vibrating transducer tip or probe; the cartridge is urged back into the first position with the springs or the magnets; there is also included: a circuit board, computing processor, a signal generator and a power source; a first magnet, a first contact pin and a first optical sensor are attached to the cartridge; a second magnet, a second contact pin and a second optical sensor are attached to the circuit board; whereby said first and second contact pins and first and second optical sensors relay orientation and position of the cartridge to the computing processor.

An assembly for vaporizing a liquid, comprising: an ultrasonic transducer with a vibrating transducer tip; a cartridge, which is preferably airtight or generally retains the liquid within the cartridge; a circuit board, computing processor, a signal generator and a power source; there are wires connecting the electrical components; a first magnet, a first contact pin and/or a first optical sensor are attached to the sealed cartridge; a second magnet, a second contact pin and/or a second optical sensor are attached to the circuit board; said first and second contact pins and first and second optical sensors relay orientation and position of the cartridge to the computing processor; the cartridge has a wick, which has a first wick end and a second wick end; the first wick end is in communication with the liquid, and when the second wick end in contact with the vibrating transducer tip, capillary action draws the liquid out of the cartridge; in a first position, the cartridge's second wick end is not in contact with the vibrating transducer tip; the cartridge is held in said first position with springs or magnets; in a second position, the cartridge's second wick end is in contact with the vibrating transducer tip, and when the ultrasonic transducer is activated, the liquid, which is drawn out though the capillary action of the wick, is atomized to create atomized liquid or a vapor, and cavitation occurs; said cavitation creates gas bubbles at the wick, forces said gas bubbles through the wick and into the cartridge and balances the pressure within the cartridge; the cartridge urged back into the first position with the springs or the magnets; whereby the ultrasonic transducer, the cartridge and the wick are arranged to allow the atomized liquid or the vapor to move in a direction away from the cartridge and the vibrating transducer tip.

All of the foregoing operational principles and advantages of the present invention will be more fully appreciated upon consideration of the following detailed description, with reference to the drawings.

BRIEF DESCRIPTION OF THE DRAWINGS

In FIG. 1, a transducer has a flat surface on one end in contact with the wick; when the cartridge is placed vertically on top of the transducer, the droplets will be expelled in all directions away from wick and transducer tip.

in FIG. 2, the transducer has a rounded end and this allows the cartridge to be placed at an angle from the vertical axis; the droplets are similarly expelled away from the wick and transducer tip.

In FIG. 5A, the cartridge is positioned away from the transducer 506 and kept in this position by magnets 523/522. Magnet 523 is attached to the cartridge 501, and magnet 522 is attached to a circuit board 520. Contact pins 521 are in contact with the circuit board 511 of the cartridge 501. An optical sensor 524 on the circuit board 520 senses that the cartridge is not in position, thus turning the transducer 506 OFF. Wires 526 from the circuit board and wires 507 from the transducer is connected to a signal generator 530 that also comprises an MCU to read the authentication chip of the cartridge.

In FIG. 5B, the cartridge 501 is pushed towards the transducer 506 so that the wick is now in contact. Sensor 524 now "sees" that the cartridge is in position to turn ON the transducer. Magnet 523 on the cartridge is now pushed away from magnet 522, such that there is now a magnetic force wanting to pull magnet 523 (and consequently the cartridge 501) back to the resting position in FIG. 5A. At least one or multiple contact pins 521 are still contacting the circuit board 511, sending the usage time and other information to the MCU on the signal generator 530 for data logging.

PARTS LISTING

Figure 1:
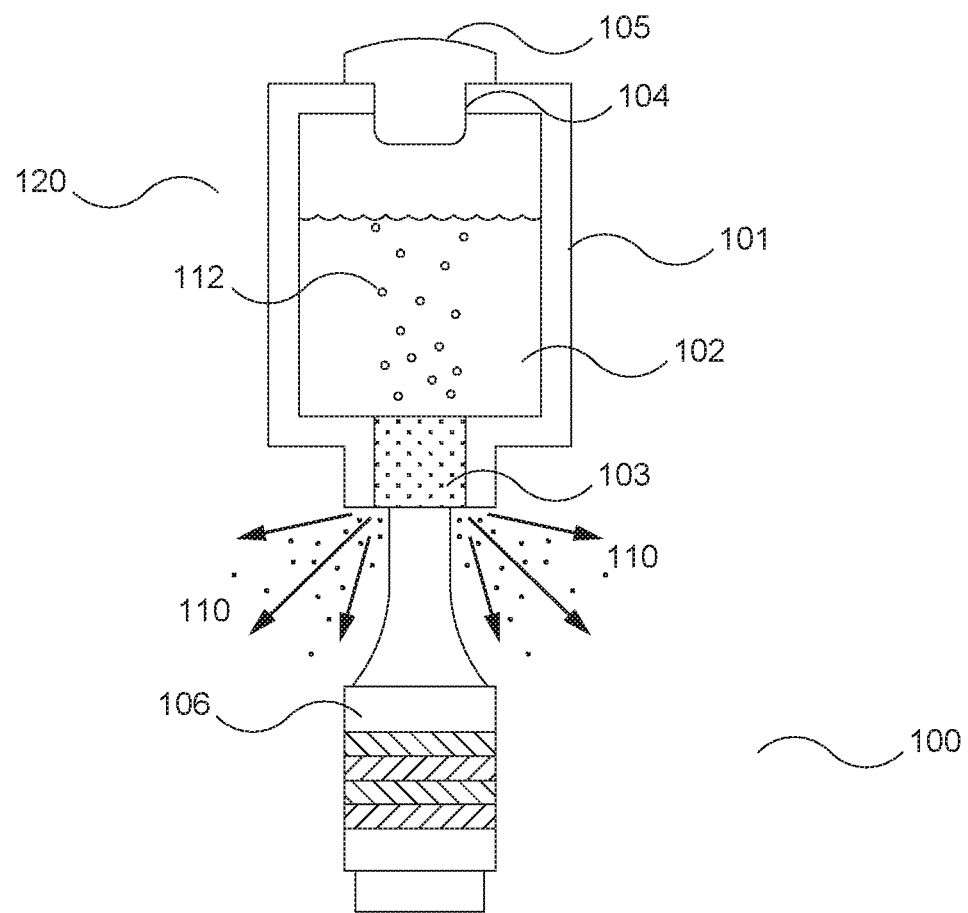
FIG. 1 is a cross-sectional view of one preferred embodiment of the invention.
Figure 2:
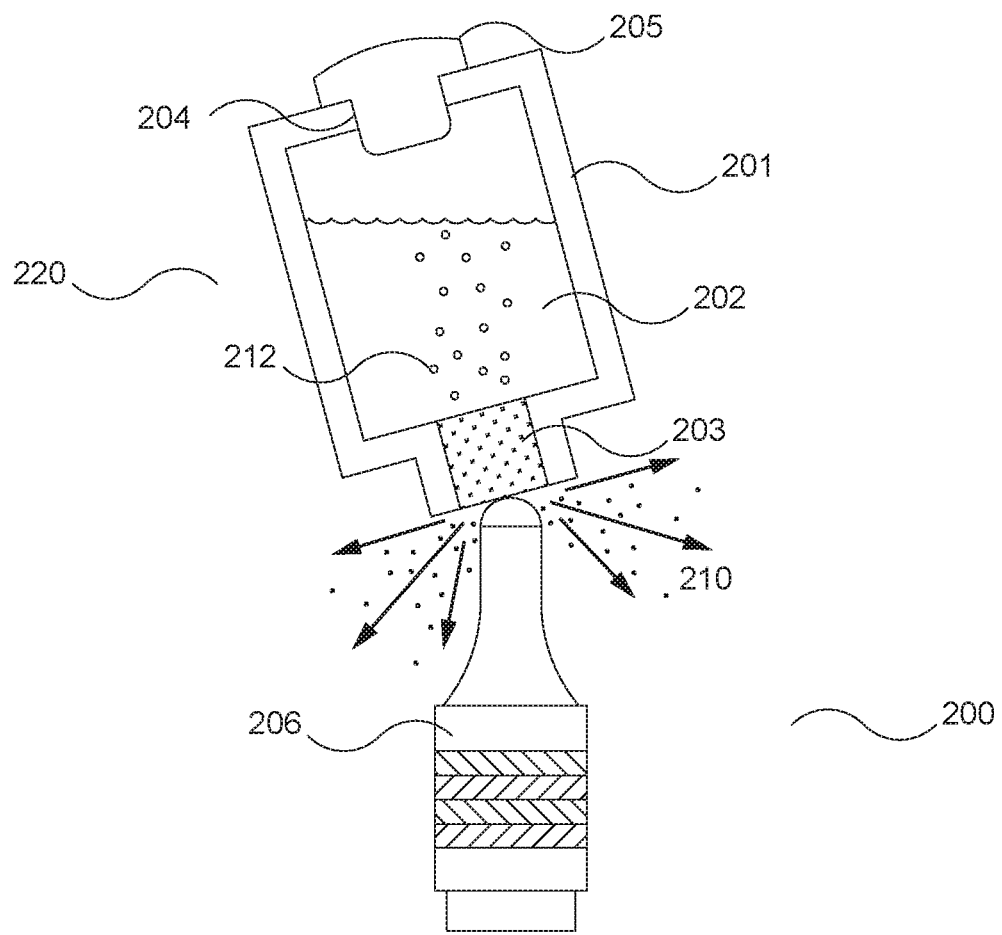
FIG. 2 a cross-sectional view of another preferred embodiment of the invention.
Figure 3:
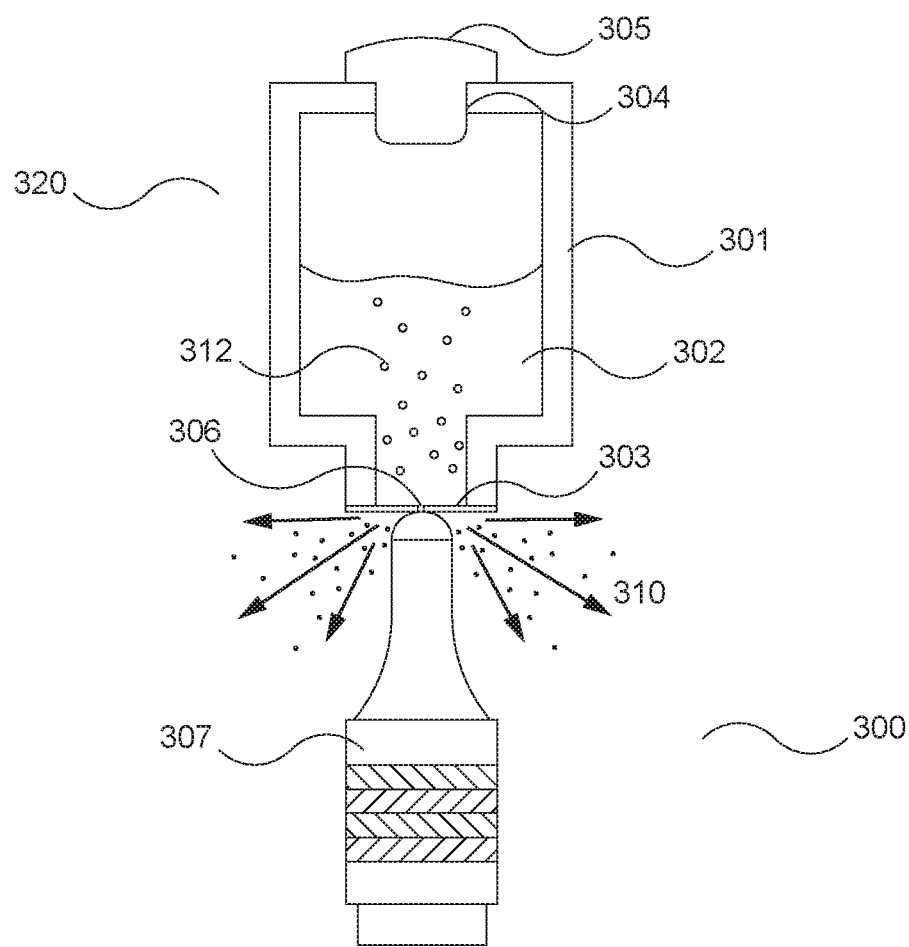
FIG. 3: Similar to the embodiment shown in FIG. 1 and FIG. 2, except for the silicone membrane 303 with a small orifice 306, and the viscous media 302. The membrane 303 can be vibrated by the transducer 306 and heat up due to vibration, which causes the temperature of the media 302 adjacent to the membrane 303 to rise, and to consequently become less viscous and to allow flow through the orifice 306 for vaporization.
Figure 4:
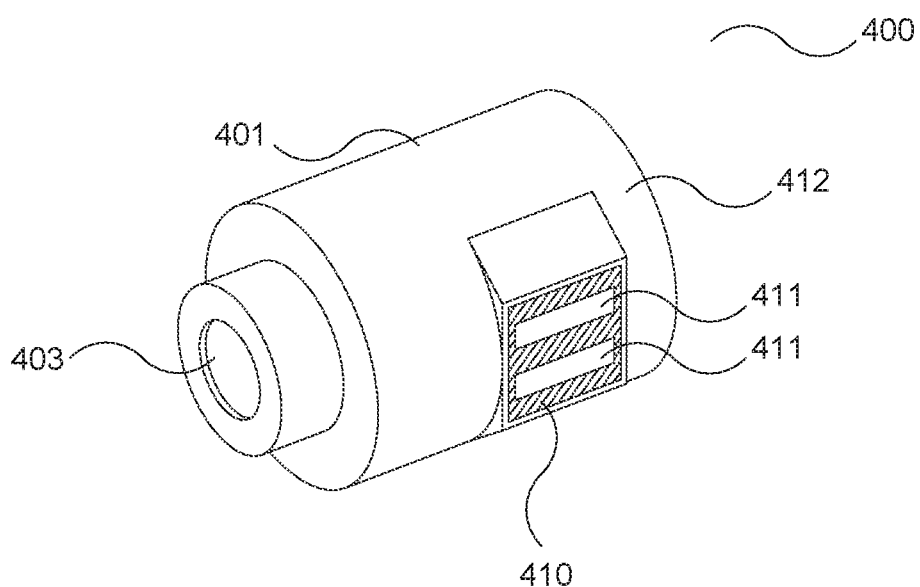
FIG. 4: Part No. 400 describes a cartridge embodiment with authentication function. A circuit board 410 is integrated with the cartridge body 401. Two contact pads 411 on the circuit board 410 provides electrical connection to the ultrasonic device to read/decode. The authentication chip is embedded in the circuit board 410.
Figure 5A:
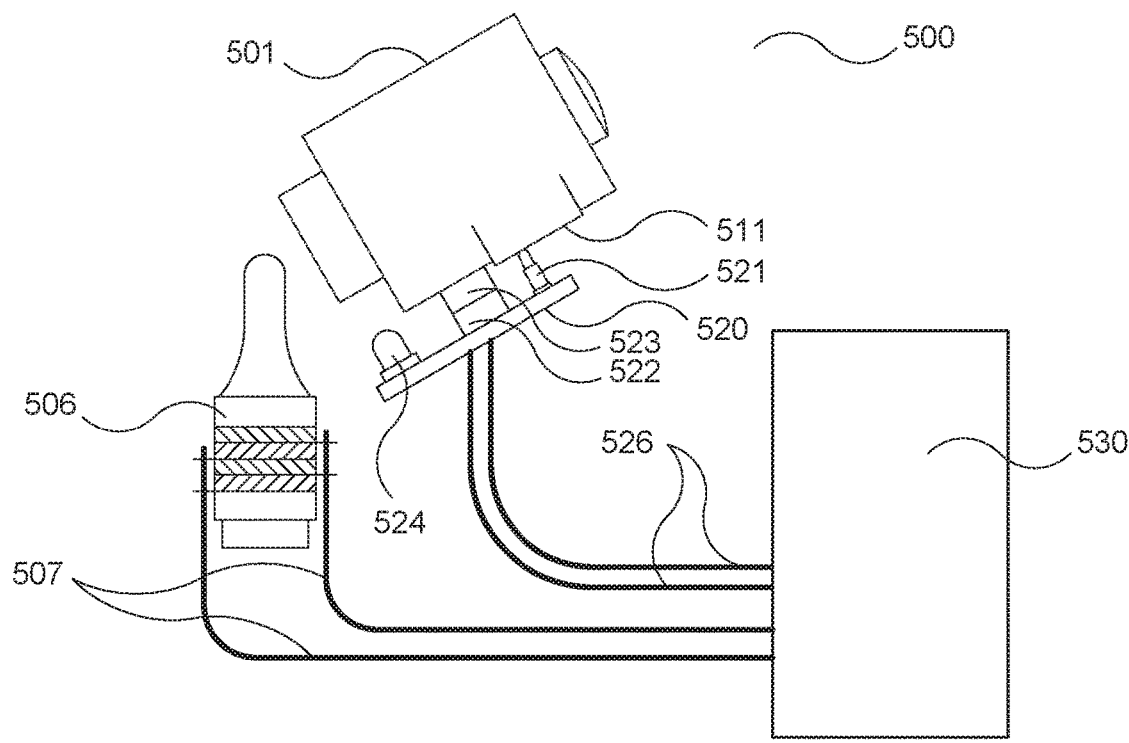
FIGS. 5A and 5B shows setup embodiments of the cartridge/transducer.
Figure 5B:
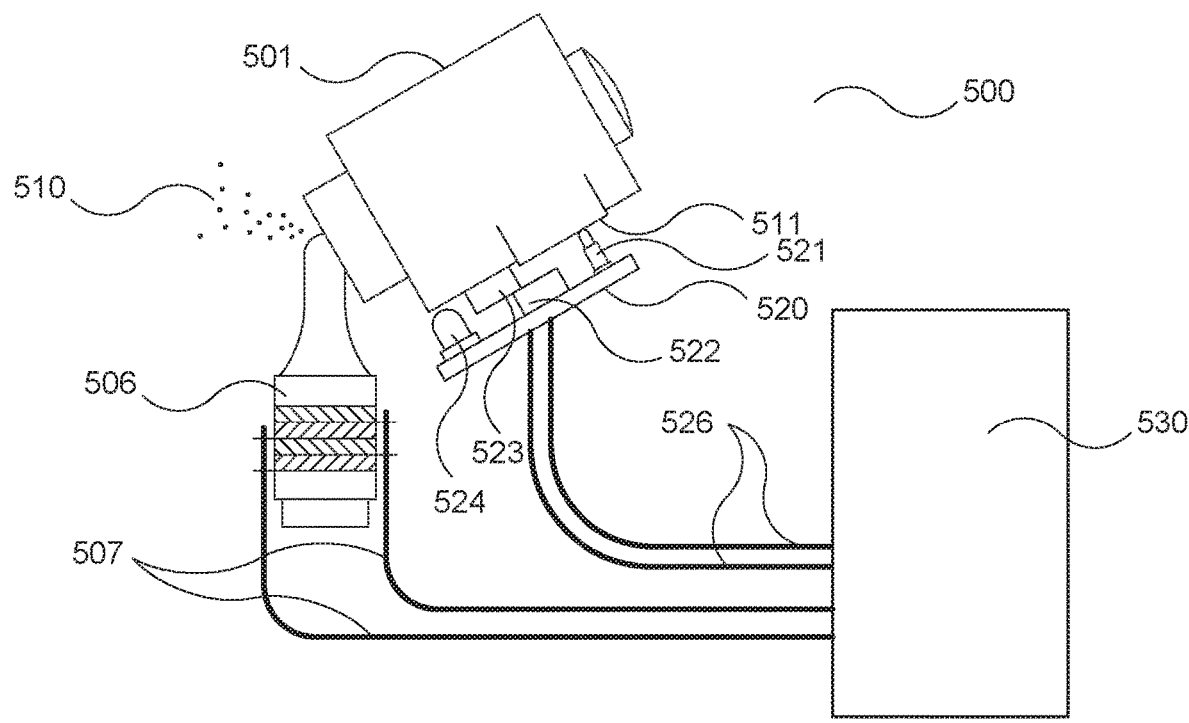
Figure 6A:
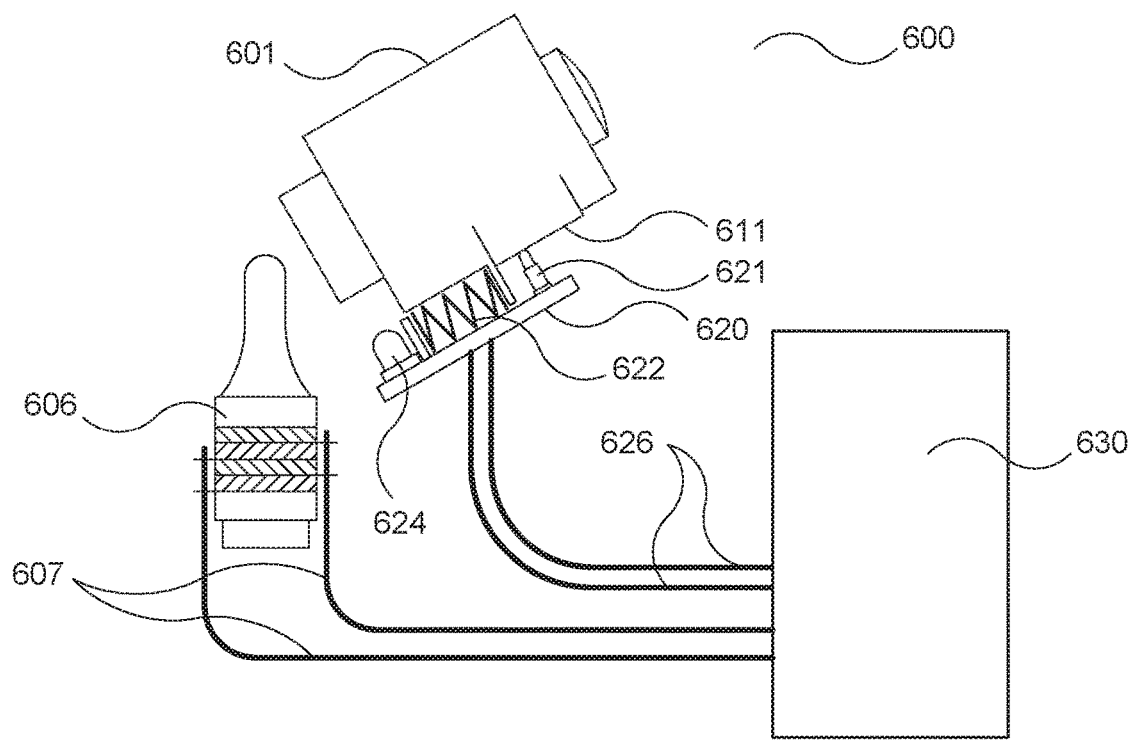
FIGS. 6A and 6B shows setup embodiments of the cartridge/transducer with use of springs instead of magnets.
Figure 6B:
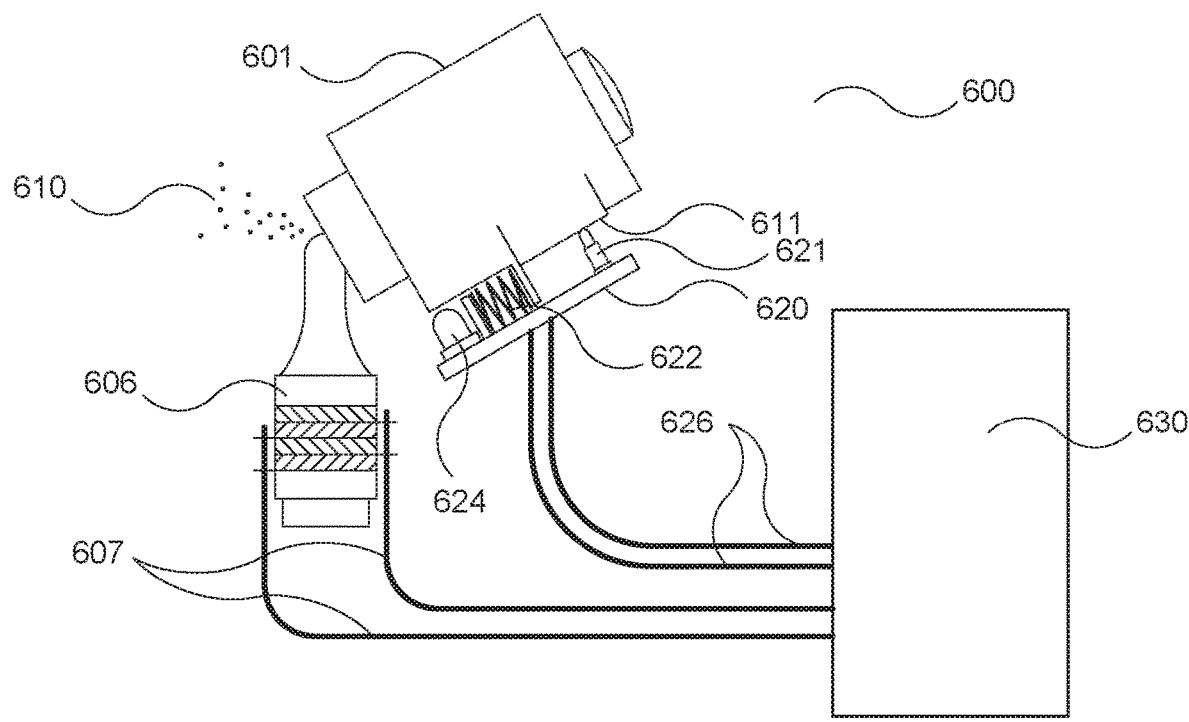

100 Atomizer
102 Liquid
103 Wick
104 Cartridge opening
105 Liquid cap
106 Transducer
110 Direction of expelled mist
112 Bubbles from cavitation
120 Cartridge assembly
200 Atomizer
201 Cartridge
202 Liquid
203 Wick
204 Cartridge opening
205 Cap
206 Transducer
210 Direction of expelled mist
212 Bubbles from cavitation
220 Cartridge assembly
300 Atomizer
301 Cartridge
302 Liquid
303 Membrane
304 Cartridge opening
305 Cao
306 Membrane opening
307 Transducer
310 Direction of expelled mist
312 Bubbles from cavitation
320 Cartridge assembly
400 Cartridge assembly 401 Cartridge housing
403 Wick
410 Circuit board
411 Electrical contact pads
412 Authentication chip
500 Atomizer
501 Cartridge
506 Transducer
507 Wires
510 Mist
511 Circuit board
520 Circuit board
521 Electrical contact pins
522/523 Magnets
524 Optical sensor/switch
526 Wires
530 Signal generator and battery
600 Atomizer
601 Cartridge
606 Transducer
607 Wires
610 Mist
611 Circuit board
620 Circuit board
621 Electrical contact pins
622 Spring
624 Optical sensor/switch
626 Wires
630 Signal generator and battery

DESCRIPTION OF THE PREFERRED
EMBODIMENTS

According to the present invention, there is provided an atomizer for the dispersal of a liquid; the atomizer uses an enclosed removable cartridge assembly with a reservoir of liquid; a wick with one end in communication with the liquid; and a vibrating transducer in contact with another end of the wick; the cartridge, wick and transducer are arranged to allow a capillary volume of liquid from the wick to vibrate together and to disperse the liquid in a direction away from the wick, so that the vapor can escape and be inhaled by the user.

Further, the reservoir may have a pluggable opening to allow filling of liquid, or the liquid can be pre-filled and completely sealed without any opening for refilling. When the wick made wet by the liquid, there is limited or no air exchange with the outside environment.

When the atomizer is inactive, the reservoir is able to hold the liquid without the liquid dripping out through the fibrous wick material. This phenomenon is similar to a drinking straw holding a volume of water with one end covered by a finger-tip. Without air entering the reservoir, the outside air pressure creates an upward force on the liquid on the wick greater than the force of gravity pulling down on the liquid. Surface tension of the fibrous wick material also creates capillary forces to keep the liquid from dripping out of the reservoir.

The volume of the reservoir is calculated such that capillary forces and atmospheric pressure is able to support the weight of the liquid, even when the reservoir is completely full. This volume equates to the weight of the liquid at any amount less than one atmosphere pressure at sea level. If the liquid is heavier than one atmosphere, it will overcome the air pressure outside the reservoir and leak out.

When the wick is placed on the transducer, liquid flows within the capillary space between the wick and transducer. As the transducer is activated, the liquid is expelled in the form of droplets from the capillary space between the wick and transducer as depicted by the arrows 110 and 210. In FIG. 1, a transducer has a flat surface on one end in contact with the wick. When the cartridge is placed vertically on top of the transducer, the droplets will be expelled in all directions away from wick and transducer tip.

In FIG. 2, the transducer has a rounded end, and this rounded shape of the transducer allows the cartridge to be placed at an angle from the vertical axis. The droplets are similarly expelled away from the wick and transducer tip. It is important to note that the atomized liquid is not dispersed through any orifice as described in the prior art, but rather, between the capillary space of the wick and transducer.

As liquid is atomized and expelled, a phenomenon known as cavitation occurs. Microscopic gas bubbles in the liquid are forced to oscillate due to the applied acoustic field from the transducer. As the bubbles collapse, droplets are expelled. At the same time, the gas from the collapsed bubbles is forced through the wick and enters the reservoir. These gas bubbles take up the volume of the liquid that are dispersed and allows more liquid to flow out of the reservoir constantly. Thus, the pressure inside the reservoir is always kept at equilibrium, even when the liquid level drops as it is being dispersed. When the transducer is turned off, no bubbles enter the reservoir, and liquid continues to be held within the reservoir.

Thus, with the construction described above, a low-cost reservoir or cartridge can be manufactured and cheaply replaced without the need for washing or sterilization. The invention therefore provides a simple, cost-effective and reliable atomizer with constant vapor output in comparison with the prior art.

The atomizer is suitable for use with any liquid to be atomized. In particular, it may be used for products such as medicine, fragrances, pesticides, detergents, malodor counteractants, water (for a humidifier), or any other type of liquid or combination of liquids dispersed by atomization. It is understood that this atomizer is suitable for liquids that are more viscous than water.

According to one embodiment, the wick is made of any fibrous material that allows the good rate of liquid flow to be dispersed by the transducer. The preferred rate is 100 mg per minute or more. A high temperature material for the fibers, such as PET (Polyethylene Terephthalate), nylon or glass is preferred, since the vibrating transducer causes friction against the wick and may melt low temperature plastic polymers. Ceramic wicks can also be used. Cotton wicks can also be used because they do not melt.

Alternatively, a plurality of fibrous materials can be used. For example, the wick can be made from two or multiple layers of material. On one end of the wick, a high temperature thin glass fiber layer is used for contacting the transducer, and a thicker low temperature material with good capillary flow on the other end to absorb liquid from the reservoir.

The reservoir can be made of plastic, glass, ceramic or metal, although transparency is preferred so a user can see the remaining volume of liquid inside the reservoir.

It is also preferred according to the present invention that the transducer is a piezo electric transducer, including without limitation: a Langevin type transducer. The transducer is connected to a control circuit and a suitable power source, preferably a battery, is provided to power the transducer. The activation of the transducer may be determined by the user by activating an appropriate activation switch.

An apparatus for vaporizing a liquid comprising: a cartridge with a first end and a second end; the first end of the cartridge is a fill end; the second end of the cartridge having a wick; the cartridge holding the liquid; without being limiting, a Langevin type transducer (horn, piezo, anvil) being in contact with the wick; a power source and a signal generator are connected to the Langevin type transducer; whereby the Langevin type transducer is activated and vibrates to cause gas bubbles to be forced into the wick and the liquid, which contacts the transducer, is atomized, and the atomized liquid is a vapor.

The cartridge can be sealed; the wick can be cotton, glass fiber, ceramic, polypropylene, polyethylene, nylon, wood, paper, felt, or porous plastics; the viscosity of the liquid is more than water.

Additional Improvements:

1. Authentication chip:

In conjunction with the microprocessor and computing device on the main vaporizer apparatus, there can be an authentication chip on the cartridge to allow for verification of the cartridge for the correct type or authorized type of vaporizer; this chip can also be used with the main vaporizer's microprocessor to log in a specific user, record and document usage, including time of use, frequency and dosage used.

The microprocessor uses encryption software to keep the vaporizer's user and usage information confidential; password access; the microprocessor chip can record the user's name, date of birth, identification code and bio-characteristics (gender, weight, age, height, etc.).

The cartridge chip also allows for communicating to the vaporizer's microprocessor chip, which can keep a log of the cartridge contents and usage; for example, the chip on the cartridge can relay the level of contents within the cartridge, which enables the user to be alerted to when the cartridge needs to be replaced or reordered.

As described, the chip on the cartridge will have an encoded profile of the contents of the cartridge, such as manufacturer, type of liquid etc. The device will keep a log of usage of the cartridge, such as when it is turned on/off, and any errors. Therefore, a profile of the cartridge use can be generated, and prevents non-genuine cartridges from being used.

2. Silicone membrane (with opening) instead of wick for very viscous fluids that do not easily flow through the pores of a wick.

In addition to the wicks mentioned earlier in this application, the cartridge can also be capped off with a silicone membrane webbing or porous opening. The silicone web will allow very viscous fluids or substances to pass through the web to the transducer.

3. Transducer tip can also be rounded instead of flat.

4. Cartridge can be angled between 0-90 degrees (vertical to horizontal) against the tip.

5. Different positions for the Cartridge:

Cartridge can be positioned so it moves towards the tip during vaporization, and away when not in use. For example, a first or resting position, wherein the cartridge does not contact the tip of the transducer; a second or active position, wherein the cartridge is moved so that the cartridge's web or wick contacts the tip of the transducer. The first or resting position prevents capillary action between the wick and tip when not in use that may cause unwanted flow/leak. The movement from a first to a second position can be controlled by springs or magnets.

6. Activation:

The unit can be activated with an on/off button; in addition, the power on/off activation can be done with a sensor/switch, so that when the cartridge is depressed (into the second or active position), the unit is activated so that there is one action rather than having to power on the transducer and depress the cartridge at the same time.

Activation can also be synchronized with optical sensors or contact pins, which allow for the microprocessor or the circuit board to determine whether the cartridge is in the first/resting position or the second/active position.

It is preferable for the apparatus to be activated when the cartridge is in the second or active position, wherein the wick on the cartridge engages the transducer probe, capillary action flows the fluid to be vaporized from within the cartridge, through the wick and to the outside of the wick for vaporization by the transducer.

Detailed embodiments of the present invention are disclosed; however, the disclosed embodiments are merely exemplary of the invention, which can be embodied in various forms; specific structural and functional details disclosed are not to be interpreted as limiting, but merely as a basis for the claims and as a representative basis for teaching one skilled in the art to variously employ the present invention in virtually any appropriately detailed structure. The title, headings, terms and phrases used are not intended to limit the subject matter or scope; but rather, to provide an understandable description of the invention. The invention is composed of several sub-parts that serve a portion of the total functionality of the invention independently and contribute to system level functionality when combined with other parts of the invention. The terms "a" or "an" are defined as: one or more than one. The term "plurality" is defined as: two or more than two. The term "another" is defined as: at least a second or more. The terms "including" and/or "having" are defined as comprising (i.e., open language). The term "coupled" is defined as connected, although not necessarily directly, and not necessarily mechanically.

Any element in a claim that does not explicitly state "means for" performing a specific function, or "step for" performing a specific function, is not be interpreted as a "means" or "step" clause as specified in 35 U.S.C. Sec. 112, Paragraph 6. In particular, the use of "step of" in the claims herein is not intended to invoke the provisions of 35 U.S.C. Sec. 112, Paragraph 6.

Incorporation by Reference: All publications, patents, patent applications and Internet website addresses mentioned in this specification are incorporated by reference to the same extent as if each individual publication, patent, or patent application was specifically and individually indicated to be incorporated by reference; U.S. Patent Appl. 61/921,906, filed on Dec. 30, 2013; 61/928,823, filed on Jan. 17, 2014; 61/928,797, filed on Jan. 17, 2014; Ser. No. 14/271,442, filed on May 6, 2014; and Ser. No. 14/272,414, filed on May 7, 2014; U.S. Pat. Nos. 6,278,218; 5,702,360; 8,257,377; 6,325,811; 5,954,736; PCT/GB2007/002863; US 2010/0044460 A1 (Sauzade); U.S. Pat. No. 5,950,619 Van Der Linden; U.S. Pat. No. 7,784,712 Wang; U.S. Pat. No. 7,975,688 Truitt; WO 2008/015394 A1 Reckitt Benckiser, which are all incorporated by reference in entirety.

We claim:

1. An assembly for vaporizing a liquid, comprising:

an ultrasonic transducer with a vibrating transducer tip;

a cartridge, which holds the liquid; the cartridge has a wick, which has a first wick end and a second wick end;

the first wick end is in communication with the liquid, and when the second wick end is contact with the vibrating transducer tip, capillary action draws the liquid out of the cartridge;

when the ultrasonic transducer is activated, the liquid, which is drawn out though the capillary action of the wick, is atomized to create atomized liquid or a vapor, and cavitation occurs;

said cavitation creates gas bubbles at the wick, forces said gas bubbles through the wick and into the sealed cartridge and balances the pressure within the cartridge;

wherein in a first position, the cartridge's second wick end is not in contact with the vibrating transducer tip; the cartridge is held in said first position with springs or magnets; wherein in a second position, the cartridge's second wick end is in contact with the vibrating transducer tip; the cartridge is configured to be urged back into the first position with the springs or the magnet;

whereby the ultrasonic transducer, the sealed cartridge and the wick are arranged to allow the atomized liquid or the vapor to move in a direction away from the cartridge and the vibrating transducer tip.

2. The assembly for vaporizing a liquid of claim 1, wherein the wick is a thin membrane of cotton, ceramic or glass fibers.

3. The assembly for vaporizing a liquid of claim 1, wherein the wick is a porous silicone membrane.

4. The assembly for vaporizing a liquid of claim 1, wherein the sealed cartridge is removable and has an authentication chip to allow for verification of the cartridge for use with authorized types of vaporizers.

5. The assembly for vaporizing a liquid of claim 1, further comprising:
a circuit board, computing processor, a signal generator and a power source;
a first magnet, a first contact pin and a first optical sensor are attached to the cartridge;
a second magnet, a second contact pin and a second optical sensor are attached to the circuit board;
whereby said first and second contact pins and first and second optical sensors relay orientation and position of the cartridge to the computing processor.

6. An assembly for vaporizing a liquid, comprising:
an ultrasonic transducer with a vibrating transducer tip;
a cartridge, which holds the liquid;
a circuit board, computing processor, a signal generator and a power source;
a first magnet, a first contact pin and a first optical sensor are attached to the sealed cartridge;
a second magnet, a second contact pin and a second optical sensor are attached to the circuit board;
said first and second contact pins and first and second optical sensors relay orientation and position of the cartridge to the computing processor;
the cartridge has a wick, which has a first wick end and a second wick end;
the first wick end is in communication with the liquid, and
when the second wick end in contact with the vibrating transducer tip, capillary action draws the liquid out of the cartridge;
wherein in a first position, the cartridge's second wick end is not in contact with the vibrating transducer tip; the cartridge is held in said first position with springs or magnets; wherein in a second position, the cartridge's second wick end is in contact with the vibrating transducer tip, and
when the ultrasonic transducer is activated, the liquid, which is drawn out though the capillary action of the wick, is atomized to create atomized liquid or a vapor, and cavitation occurs; said cavitation creates gas bubbles at the wick, forces said gas bubbles through the wick and into the cartridge and balances the pressure within the cartridge;
the cartridge is configured to be urged back into the first position with the springs or the magnets;
whereby the ultrasonic transducer, the cartridge and the wick are arranged to allow the atomized liquid or the vapor to move in a direction away from the cartridge and the vibrating transducer tip.

7. The assembly for vaporizing a liquid of claim 6, wherein the wick is a thin membrane of cotton, ceramic or glass fibers.

8. The assembly for vaporizing a liquid of claim 6, wherein the wick is a porous silicone membrane.

9. The assembly for vaporizing a liquid of claim 6, wherein the cartridge is sealed and removable and has an authentication chip to allow for verification of the cartridge for use with authorized types of vaporizers.

* * * * *